(12) United States Patent
Kamo et al.

(10) Patent No.: US 9,216,187 B2
(45) Date of Patent: Dec. 22, 2015

(54) SOYASAPOGENOL COMPOSITION

(71) Applicant: J-OIL MILLS, INC., Tokyo (JP)

(72) Inventors: Shuichi Kamo, Tokyo (JP); Toshiro Sato, Tokyo (JP); Shunsuke Suzuki, Tokyo (JP)

(73) Assignee: J-Oil Mills, Inc., Tokyo (JP)

( * ) Notice: Subject to any disclaimer, the term of this patent is extended or adjusted under 35 U.S.C. 154(b) by 0 days.

(21) Appl. No.: 14/135,768

(22) Filed: Dec. 20, 2013

(65) Prior Publication Data

US 2014/0121177 A1    May 1, 2014

Related U.S. Application Data

(63) Continuation of application No. PCT/JP2012/059845, filed on Apr. 11, 2012.

(30) Foreign Application Priority Data

Jun. 28, 2011 (JP) .................. 2011-142434

(51) Int. Cl.
| | |
|---|---|
| *A61K 31/70* | (2006.01) |
| *A61K 31/704* | (2006.01) |
| *A61K 8/60* | (2006.01) |
| *A61K 8/63* | (2006.01) |
| *A61Q 19/06* | (2006.01) |
| *A61K 31/045* | (2006.01) |
| *A61K 31/047* | (2006.01) |
| *C07J 63/00* | (2006.01) |
| *A23L 1/30* | (2006.01) |
| *A61K 8/34* | (2006.01) |
| *A61K 31/05* | (2006.01) |
| *A61Q 19/00* | (2006.01) |

(52) U.S. Cl.
CPC .............. *A61K 31/704* (2013.01); *A23L 1/30* (2013.01); *A61K 8/347* (2013.01); *A61K 8/60* (2013.01); *A61K 8/63* (2013.01); *A61K 31/045* (2013.01); *A61K 31/047* (2013.01); *A61K 31/05* (2013.01); *A61Q 19/00* (2013.01); *A61Q 19/06* (2013.01); *C07J 63/00* (2013.01); *A61K 2800/5922* (2013.01); *A61K 2800/92* (2013.01)

(58) Field of Classification Search
CPC ....... A61K 31/704; A61K 8/60; A61K 8/347; A23L 1/30
See application file for complete search history.

(56) References Cited

U.S. PATENT DOCUMENTS

2006/0275862 A1    12/2006    Watanabe et al.

FOREIGN PATENT DOCUMENTS

| JP | H10234396 A | 9/1998 |
|---|---|---|
| JP | 2000078955 A | 3/2000 |
| JP | 2003189831 A | 7/2003 |
| JP | 2005137201 A | 6/2005 |
| JP | 2006213649 A | 8/2006 |
| JP | 2009132739 A1 | 6/2009 |
| JP | 2009209066 A | 9/2009 |
| JP | 2010275312 A | 12/2010 |
| WO | 2008155890 | 12/2008 |
| WO | 2010150612 A1 | 12/2010 |

OTHER PUBLICATIONS

Yoshiki et al., "Relationship Between Chemical Structures and Biological Activities of Triterpenoid Saponins from Soybean", Biosci. Biotechnol. Biochem., vol. 62, pp. 2291-2299, 1998.

Kawano et al., "Effect of Soya Saponins on Gold Thioglucose (GTG)-Induced Obese Mice", International Journal of Obesity, vol. 10, pp. 293-302, 1986.

Nakashima et al., "Inhibitory effect of glycosides like saponin from soybean on the infectivity of HIV in vitro", AIDS, vol. 3, pp. 655-658, 1989.

Tanaka et al., "Hypoglycemic Effect of Soyasaponin B Extracted from Hypocotyl on the Increasing Blood Glucose in Diabetic Mice", Journal of Japanese Society of Clinical Nutrition, vol. 27, (4), pp. 358-366, 2006.

Izumi et al., "Soy Isoflavone Aglycones Are Absorbed Faster and in Higher Amounts than Their Glucosides in Humans", American Society for Nutritional Sciences, pp. 1695-1699, 2000.

Zubik et al., Bioavailability of soybean isoflavones from aglycone and glucoside forms in American women, American Journal Clinical Nutrition, pp. 1459-1465, 2003.

Gurfinkel et al., "The isolation of soyasaponins by fractional precipitation, solid phase extraction, and low pressure liquid chromatography"International Journal of Food Sciences and Nutrition, vol. 56, No. 7, pp. 501-519, Nov. 2005.

Ikeda et al., "Partial Hydrolysis of Soyasaponin I and the Hepatoprotective Effects of the Hydrolytic Products. Study of the Structure-Hepatoprotective Relationship of Soyasapogenol B Analogs", Chem. Pharm. Bulletin, vol. 46, No. 2, pp. 359-361, 1998.

International Search Report, PCT/JP2012/059845, Jun. 21, 2012, 6 pages.

*Primary Examiner* — Elli Peselev

(74) *Attorney, Agent, or Firm* — Edell, Shapiro & Finnan, LLC

(57) ABSTRACT

A soy saponin composition is provided high bodily absorption characteristics. In an embodiment, a soyasapogenol composition comprises soyasapogenol B and 3-O-D-glucuronopyranosyl soyasapogenol B. The weight ratio (B/A) of the 3-O-D-glucuronopyranosyl soyasapogenol B to the soyasapogenol B is in the range of 0.001-10. The composition can be produced by partial decomposition of a sugar chain residue of a soy saponin B group glycoside utilizing an acid.

7 Claims, 2 Drawing Sheets

SOYASAPOGENOL COMPOSITION

TECHNICAL FIELD

The present invention relates to a soyasapogenol composition, a production process for the same, and a usage of the same and, more specifically, to a composition which is improved in absorption of soyasapogenol B and the like.

BACKGROUND

Saponin is an amorphous glycoside which is abundantly present in soybeans, azuki beans, olive, and the like. Saponin is named since it has a hydrophobic portion and a hydrophilic portion and forms persistent bubbles when mixed with water and shaken.

Saponin is broadly classified into steroid saponin and triterpenoid saponin according to the type of aglycone. The soyasaponin is contained abundantly in soybeans (glycine max), particularly in a soybean hypocotyl, and is a kind of the triterpenoid saponin Soyasaponins are mainly composed of soyasaponin Aa, Ab, Ac, Ad, Ae, Af, Ag, and Ah each having soyasapogenol A as the aglycone (hereinafter referred to as "soyasaponin group A glycoside") and soyasaponin I, II, III, IV, and V each having soyasapogenol B as the aglycone (hereinafter referred to as soyasaponin group B glycoside) (Non-Patent Literature 1).

As the efficacies of soyasaponins, anti-obesity, blood neutral lipid reduction, cholesterol lowering effect, hepatoprotective action, antiviral activity, and the like have been known.

Soyasaponins having a high group B content are more effective for suppressing an increase in blood neutral lipid as compared to soyasaponins having a high group A content. The effect of suppressing blood glucose level increase is not observed with soyasaponin group A but is observed with soyasaponin B group. It is considered that the reason for the high activity of the soyasaponin group B resides in the absorption of the group B which is higher than that of the group A.

Soyasaponin aglycone obtained by removing sugar chain residues from soyasaponins is known to have a hyaluronic acid production promotion effect and a melanin production suppression effect of skin cells as well as a collagen production promotion effect. Also, 3-O-D-glucuronopyranosyl soyasapogenol B in which glucuronic acid is attached to the aglycone is known to have an anti-oxidant ability.

A further improvement in bioactivity can be expected from a further improvement in absorption of the soyasaponin group B. In order to improve the absorption of soyasaponin B group, it is contemplated to change the glycoside of the soyasaponin group B to the aglycone, i.e. to soyasapogenol B. As methods for producing the soyasapogenol B, a method using high pressure hot water, a method utilizing enzymatic decomposition, a chemical synthesis method, and the like are known.

However, in comparison of absorption between glycoside and aglycone of soybean isoflavone, it has been reported that aglycone has better absorption, and, on the other hand, it has been reported that there is no difference in absorbance. Whether there is the difference in absorption between glycoside and aglycone of soyasaponin or not has not been investigated yet.

SUMMARY

As previously noted, the improvement in absorption of soyasaponin has not been known. Therefore, an object of the present invention is to provide a soyasaponin composition having high absorption.

In accordance with embodiments of the present invention in relation to the improvement of absorption of soyasaponin group B, it has been determined that soyasapogenol B which is aglycone of soyasaponin group B has higher absorption than soyasaponin group B glycoside and that soyasapogenol B has higher absorption than soyasapogenol A which is aglycone of a soyasaponin group A glycoside. It has further been determined, in accordance with embodiments of the present invention, that a composition containing the soyasapogenol B and 3-O-D-glucuronopyranosyl soyasapogenol B is much more improved in absorption as compared to a single dose of the glycoside or aglycone of soyasaponin to accomplish the present invention.

The present invention provides a soyasapogenol composition comprising soyasapogenol B represented by the following Formula A:

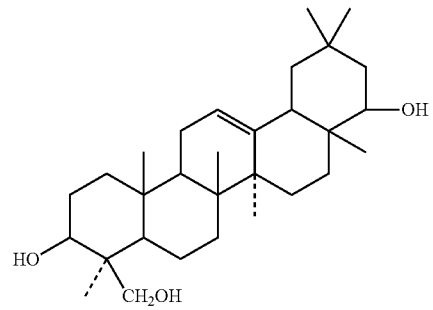

and 3-O-D-glucuronopyranosyl soyasapogenol B represented by the following Formula B:

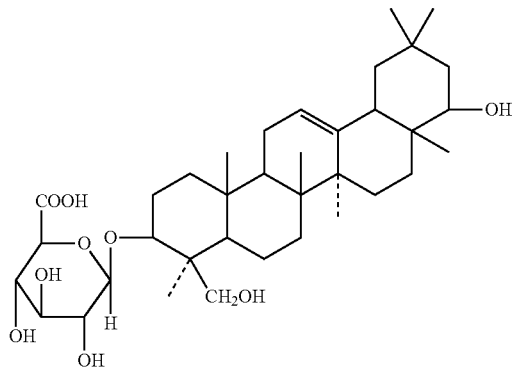

wherein a weight ratio (B/A) of the component (B) to the component (A) is 0.001 to 10.

Preparation Example 1 of International Patent Application Publication No. WO 2008/155890 describes production of soyasapogenol B by way of acid decomposition of soyasaponin glycoside. However, 3-O-D-glucuronopyranosyl soyasapogenol B is not detected from the obtained soyasapogenol powder. In other words, the soyasapogenol composition which contains both of soyasapogenol B and 3-O-D-glucuronopyranosyl soyasapogenol B has not been known in the conventional art. The composition of the present invention is not present in traditional soybean foods such as a bean curd, soy milk, soybean flour, a fermented soybean paste, and soy sauce and soybean materials which are obtained by treating a soybean protein in an extruder, followed by extraction with an organic solvent such as ethanol, methanol, and butanol.

The composition of the present invention may preferably contain the component (A) and the component (B) in an amount of 0.05 to 100 wt % of the composition in terms of soyasapogenol.

The present invention also provides a process for producing the soyasapogenol composition, comprising partially decomposing a sugar chain residue of soyasaponin group B glycoside by acid. Since the soyasapogenol composition containing both of the component (A) and the component (B) is not known in the conventional art, the production process is also novel.

For the partial decomposition, a material containing 5 wt % or more of the soyasaponin group B glycoside may preferably be used.

The present invention also provides a drug comprising the soyasapogenol composition and having at least one efficacy selected from the group consisting of suppression of blood glucose level increase, suppression of blood pressure increase, lipid metabolism improvement, cholesterol lowering action, metabolic syndrome improving action, suppression of food intake, obesity prevention, anti-allergic action, immunostimulative action, adjuvant activity, anti-inflammatory action, antitumor activity, anti-ulcer activity, hepatoprotective action, epithelium cell proliferation suppression, cell membrane permeability acceleration, cell activating action, antiviral activity, anti-HIV activity, antimutagenic activity, platelet coagulation suppressing action, anticomplementary activity, hyaluronic acid production promotion and melanin production suppression of skin cells, collagen production promotion, anti-oxidation action, kidney stone prevention, and suppression of development of dementia.

The present invention also provides a food or a supplement comprising the soyasapogenol composition.

The present invention also provides a cosmetic material comprising the soyasapogenol composition.

The composition of the present invention comprising soyasapogenol B and 3-O-D-glucuronopyranosyl soyasapogenol B is a saponin composition having high absorption, i.e. having high bioavailability.

The composition of the present invention exhibits physiological activity based on soyasapogenol B in vivo with a smaller amount of dose. Since the composition of the present invention is a component derived from soybean, which is a natural plant, and is administered at a smaller dose than conventional examples, it is possible to continuously take the composition for a long period. Therefore, the composition of the present invention is remarkably industrially advantageous soyasaponin.

According to the production process of the composition of the present invention comprising partially decomposing a sugar chain residue of the soyasaponin group B glycoside by acid, the composition is easily produced. Further, the process is excellent in easy adjustment of the ratio between soyasapogenol B and 3-O-D-glucuronopyranosyl soyasapogenol B.

DETAILED DESCRIPTION

Figure 1A:
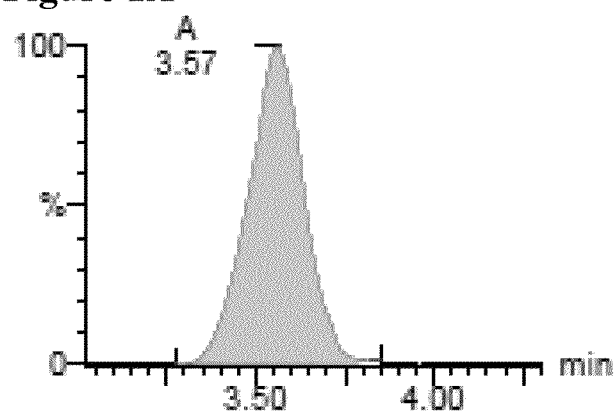
FIG. 1A is a diagram showing a chart of a chromatogram of soyasapogenol A (indicated as A in the drawing)

Hereinafter, embodiments of the present invention will be described in more detail. The composition of the present invention essentially contains soyasapogenol B represented by Formula A:

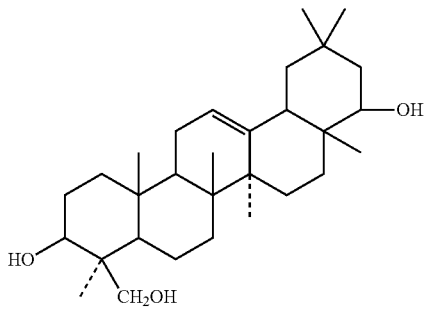

(hereinafter referred to as component (A)).

Further, the composition of the present invention essentially contains 3-O-D-glucuronopyranosyl soyasapogenol B represented by Formula B:

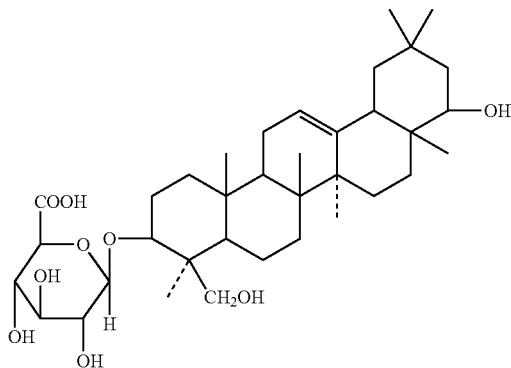

(hereinafter referred to as component (B)). The component (B) is a glycoside in which glucuronic acid is bound to the chemical structure of the component (A).

A weight ratio (B/A) of the component (B) to the component (A) may be 0.001 to 10, preferably 0.01 to 5, more preferably 0.01 to 3, furthermore preferably 0.1 to 2.5, most preferably 0.25 to 2.5. When the B/A value is less than 0.001, it is difficult to expect an improvement in absorption of the soyasapogenol B. In contrast, when the B/A value is higher than 10, the improvement in absorption of soyasapogenol B is saturated or lowered.

The content of the component (A) and the component (B) in the composition of the present invention may ordinarily be, in terms of soyasapogenol, 0.05 to 100 wt %, preferably 0.5 to 100 wt %, more preferably 2.5 to 100 wt %.

The present invention also provides a process for producing the composition. In the process, partial acid decomposition of a sugar chain residue of soyasaponin group B glycoside, DDMP glycoside, or soyasaponin group E glycoside represented by the following Formula:

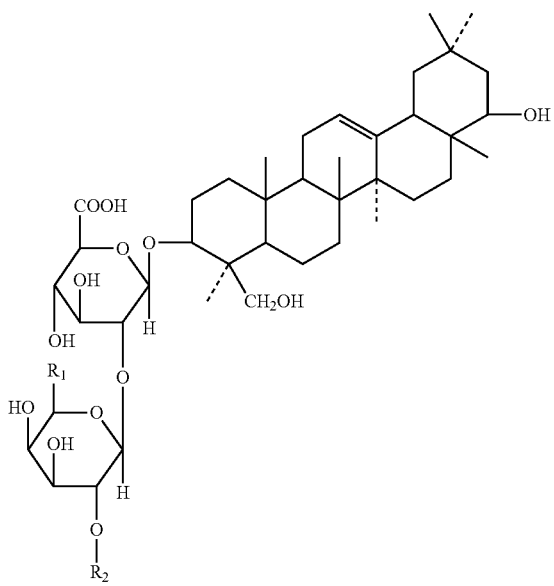

| Group B | $R_1$ | $R_2$ |
|---|---|---|
| Soyasaponin Ba (V) | $CH_2OH$ | β-D-Glc |
| Soyasaponin Bb (I) | $CH_2OH$ | α-L-Rha |
| Soyasaponin Bc (II) | H | α-L-Rha |
| Soyasaponin Bb' (III) | $CH_2OH$ | H |
| Soyasaponin Bc' (IV) | H | H |

Glc . . . glucose
Rha . . . rhamnose is performed, so that the component (A) from which the sugar chain residue is completely removed and the component (B) left by glucuronic acid of the sugar chain reside are simultaneously produced at the predetermined weight ratio. Soyasaponin group B glycoside is preferred from the viewpoint of material stability.

It is possible to extract soyasaponin group B glycoside or soyasaponin glycoside containing soyasaponin group B glycoside from hypocotyl, cotyledon, and whole grains of soybeans by known methods such as WO2003/075939. As the material to be subjected to the acid decomposition, the one containing the soyasaponin group B glycoside in an amount ordinarily of 5 wt % or more, preferably 15 to 100 wt %, more preferably 30 to 100 wt %, may be used. As soyasaponin glycoside, those which are commercially available are usable without particular limitation. For example, Saponin AZ-B (product name, manufactured by J-OIL MILLS, INC.) is preferred as the material since soyasaponin group B glycoside thereof is increased to 50 to 100 wt % as compared to the conventional materials.

After dissolving the soyasaponin glycoside into organic solvent such as ethanol, methanol, and butanol, acid such as sulfuric acid, hydrochloric acid, and nitric acid is added. As another method, soyasaponin glycoside is added to and dissolved into a reaction solvent obtained by diluting the acid with water, ethanol, methanol, butanol, ethyl acetate, or the like. Preferably, the acid is added after the soyasaponin glycoside is dissolved into the organic solvent from the viewpoints that a yield and a recovery rate of the composition are increased and that the composition is collected in a short time with this method.

A concentration of the acid may ordinarily be 1 to 55 wt %, preferably 3 to 25 wt %, relative to the reaction solution. When the acid concentration is lower than 1 wt %, the component B is scarcely obtained, resulting in a composition having a considerably low weight in some cases. In contrast, when the acid concentration is higher than 60 wt %, the yields of the component A and the component B are reduced, resulting in a considerably low concentration in terms of aglycone in some cases.

The acid decomposition is started by heating the solution to which the acid is added. An acid decomposition temperature is appropriately selected based on the type and concentration of the acid, a degree of the partial decomposition (i.e. B/A), and the like. The acid decomposition temperature may ordinarily be from a room temperature to 150° C., preferably 50° C. to 80° C. An acid decomposition time may ordinarily be 0.5 to 23 hours, particularly 1 to 6 hours, though it depends on the acid decomposition temperature.

A degree of progress of the partial decomposition is detected by using an appropriate detector (e.g. sampling and chromatography), and when the predetermined B/A weight ratio is achieved the solution is neutralized by using a base such as sodium hydroxide, potassium hydroxide, sodium carbonate, sodium hydrogencarbonate, and potassium hydrogencarbonate.

A solid phase of the neutralized product contains the component (A) and the component (B), and a water phase thereof contains a sugar which was bound to the glycoside. The solid phase containing the component (A) and the component (B) is collected by subjecting the neutralized product to centrifugation, filtration, spontaneous sedimentation, filter pressing, or the like. The collected solid phase is appropriately dried to obtain a dried product.

Apart from the components (A) and (B), the collected product can sometimes contain glycoside as material, soyasapogenol A, a protein, an oligosaccharide, a saccharide, an amino acid, a free fatty acid, triglyceride, and the like as impurities. In such a case, an appropriate purification (e.g. column chromatography, solvent fractionation, distillation, membrane separation, precipitation, etc.) may be performed to purify the components (A) and (B) from the collected product. Alternatively, the collected product as it is may be used as the composition of the present invention.

Also, the composition of the present invention may be produced by mixing the component (A) and the component (B), which are separately prepared, at the predetermined weight ratio.

Soyasapogenol B which is the component (A) is obtainable by removing a sugar chain from the soyasaponin group B glycoside by an ordinary method. More specifically, soyasaponin glycoside is subjected to an enzyme reaction by glycosidase (U.S. Patent Application No. 2006/0275862 A1), a high temperature high pressure treatment (International Patent Application Publication No. WO 2008/155890), a fermentation treatment, or the like. Soyasapogenol B may be obtained by a chemical synthesis (Japanese Patent Application No. JP 2005-137201 A). The disclosures of these and all other patent publications are incorporated herein by reference.

Examples of the process for producing the component (B) include the one in which the component (B) is isolated after obtaining the composition containing the component (A) and the component (B) by the production process of the present invention, the one in which a reaction between the soyasapogenol B and a glucuronic acid derivative is allowed in accordance with the chemical synthesis method described in International Patent Application Publication No. WO 2008/155890, and then a protecting group of the generated reaction product is desorbed, and the like.

Since the composition of the present invention has the high absorption, the efficacies of soyasapogenol B are exhibited with a lower dose as compared to the conventional examples. Examples of conventionally known efficacies include suppression of blood glucose level increase, suppression of blood pressure increase, lipid metabolism improvement, cholesterol lowering action, metabolic syndrome improving action, suppression of food intake, obesity prevention, anti-allergic action, immunostimulative action, adjuvant activity, anti-inflammatory action, antitumor activity, anti-ulcer activity, hepatoprotective action, epithelium cell proliferation suppression, cell membrane permeability acceleration, cell activating action, antiviral activity, anti-HIV activity, antimutagenic activity, platelet coagulation suppressing action, anticomplementary activity, hyaluronic acid production promotion and melanin production suppression of skin cells, collagen production promotion, anti-oxidation action, kidney stone prevention, suppression of development of dementia, and the like. Since the composition of the present invention is a component derived from soybean, which is a natural plant, and is administered at the smaller dose as compared to the conventional examples, it is possible to continuously take the composition for a long period.

The composition of the present invention is appropriately used in the form of a product such as a medical product, a functional food, a supplement, a general processed food, and a cosmetic material. An amount of the composition of the present invention to be added to the product varies depending on the form of the product and an intake amount of the product and may ordinarily be 0.001 to 100 wt %, preferably 0.003 to 100 wt %.

A third component which can be added to the composition of the present invention and has high utilization is soyasaponin other than the components (A) and (B), a diluent or a concentration adjuster, and a solubilizer. Specific examples of the soyasaponin other than the components (A) and (B) include soyasaponin group B glycoside, soyasaponin group A glycoside and aglycone thereof, and soybean isoflavone. When a starch, dextrin, cellulose, or the like is used as the diluent or the concentration adjuster, the composition of the present invention is simply dispersed thereinto. When the components (A) and (B) are subsumed by cyclodextrin, absorption of the hydrophobic components of the components is improved. Also, when the composition of the present invention is dissolved into an emulsifier or a fat, absorption of the composition is improved.

In the case of using the composition of the present invention as a drug, those generally used as auxiliary agents of drugs may be added in addition to the component (A) and the component (B). For example, depending on dosage form and method for administration, a generally used excipient, a disintegrator, a binder, a lubricant, a vitamin, a xanthine derivative, an amino acid, a pH adjuster, a refreshing agent, a suspending agent, a viscosity improver, a solubilization auxiliary agent, an antioxidant, a coating agent, a plasticizer, a surfactant, water, alcohol, a water-soluble polymer, a sweetener, a taste modifier, an acidifier, a flavoring agent, a coloring agent, or the like may be added within qualitative and quantitative ranges which do not impair the effects of the present invention.

As the form of the drug of the composition of the present invention, the composition may be processed into the form of a solid formulation such as a powder, a granule, a capsule, a pill, a tablet, a chewable tablet, and a drop; an orally administrative agent such as a liquid agent including a health drink, a solution, a suspension, an emulsion, a syrup, and a dry syrup; a percutaneously administrative agent such as a liquid agent, a solution, an emulsion, and a cream. Since soyasapogenol is in the form of a powder, the form may preferably be the solid formulation.

A method of intake in the case of the use as drug is not particularly limited. Examples thereof include oral intake, percutaneous intake, transfusion, injection (intramuscular, intra-abdominal, subcutaneous, or intravenous), and the like. The oral intake of a tablet, a capsule, or the like is preferred from the viewpoint of a lowered burden on a patient.

An amount of intake in the case of the use for drug may appropriately be set depending on a symptom. In general, a daily soyasapogenol B intake may preferably be 1 to 200 mg, more preferably 5 to 100 mg.

In the case of using the composition of the present invention as a health food, a supplement, or a general processed food, those generally used as an additive for the health food and the like may be added in addition to the component (A) and the component (B). For example, depending on the form of the orally administrative agent, a generally used excipient, a disintegrator, a binder, a lubricant, a vitamin, a xanthine derivative, an amino acid, a pH adjuster, a refreshing agent, a suspending agent, a viscosity improver, a solubilization auxiliary agent, an antioxidant, a coating agent, a plasticizer, a surfactant, water, an alcohol, a water-soluble polymer, a sweetener, a taste modifier, an acidifier, a flavoring agent, a coloring agent, or the like may be added within qualitative and quantitative ranges which do not impair the effects of the present invention.

In order to use the composition of the present invention as the supplement or the functional food, the composition is processed into the orally administrative agent such as a solid formulation including a powder, a granule, a capsule, a pill, a tablet, a chewable tablet, and a drop and a liquid agent including a health drink, a solution, a suspension, an emulsion, a syrup, and a dry syrup, for example. Since soyasapogenol is in the form of a powder, the form may preferably be the tablet.

The composition of the present invention may be added directly during processing of the general processed food such as bread, steamed rice, soup, prepared food, confectionery, and candy.

An intake amount in the case of the use as health food or supplement may be appropriately set depending on the usage. In general, a daily soyasapogenol B intake may be preferably 1 to 200 mg, more preferably 5 to 100 mg.

In the case of using the composition of the present invention as the cosmetic material, those generally used as an auxiliary agent for cosmetic materials may be added in addition to the component (A) and the component (B). Examples thereof include polyvalent alcohols such as ethylene glycol, polyethylene glycol, propylene glycol, 1,3-butylene glycol, 1,4-butylene glycol, dipropylene glycol, glycerin, diglycerin, polyglycerin, penthylene glycol, isoprene glycol, glucose, maltose, fructose, xylitol, sorbitol, maltotriose, and erythritol; lower alcohols such as methanol, ethanol, propyl alcohol, isopropyl alcohol, butyl alcohol, and isobutyl alcohol; higher fatty acids such as oleic acid, isostearic acid, lauric acid, myristic acid, palmitic acid, stearic acid, behenic acid, and undecylenic acid; oils such as olive oil, corn oil, camellia oil, macadamia nut oil, avocado oil, rapeseed oil, sesame oil, castor oil, safflower oil, cotton seed oil, jojoba oil, coconut oil, and palm oil; waxes such as carnauba wax, candelilla wax, beeswax, and lanolin; sugars such as sorbitol, mannitol, glucose, sucrose, lactose, and trehalose; viscosity improvers such as carrageenan, xanthan gum, gelatin, pectin, agarose, alginate, dextrin, methyl cellulose, ethyl cellulose, hydroxypropyl cellulose, hydroxyethyl cellulose, carboxymethyl cellulose, a carboxyvinyl polymer, polyvinyl alcohol, polyvinyl pyrrolidone, gum arabic, gum karaya, gum tragacanth, and tamarind gum; preservatives such as phenoxyethanol, methylparaben, ethylparaben, propylparaben, butylparaben, paraoxybenzoic acid ester, benzoic acid, salicylic acid and salicylate, sorbic acid and sorbate, dehydroacetic acid and dehydroacetate, chlorocresol, and hexachlorophene; nonionic surfactants such as sodium lauroyl sulfate and polyoxyethylene sorbitan monooleate; anionic surfactants such as alkyl sulfate and normal sodium dodecylbenzen sulfonate; a cationic surfactant such as polyoxyethylene dodecyl monomethyl ammonium chloride; steroidal and non-steroidal anti-inflammatory agents; vitamins such as vitamin A, vitamin D, vitamin E, vitamin F, and vitamin K or a vitamin derivative such as pyridoxine dicaprylate, pyridoxine dipalmitate, ascorbyl dipalmitate, ascorbyl monopalmitate, ascorbyl monostearate; antioxidants such as flavonoid and carotenoid; higher aliphatic hydrocarbons such as squalane, squalene, and fluid paraffin; sphingolipids such as ceramide, cerebroside, and sphingomyelin; sterols such as cholesterol and phytosterol; silicones such as methylpolysiloxane, methylphenylpolysiloxane, methylcyclopolysiloxane, octamethylcyclotetrasiloxane, octamethylcyclopentasiloxane, decamethylcyclopentasiloxane, and methylhydrogenpolysiloxane; UV absorbers such as paraaminobenzoic acid, paraaminobenzoic acid monoglycerin ester, methyl anthranilate, homomenthyl-N-acetylanthranilate, octyl paramethoxycinnamate, and ethyl-4-isopropyl cinnamate; minerals such as bentonite, smectite, beidellite, nontronite, saponite, hectorite, sauconite, and stevensite; inorganic pigments such as red iron oxide, yellow iron oxide, black iron oxide, cobalt oxide, ultramarine pigments, iron blue pigments, titanium oxide, and zinc oxide; colorants such as Red No. 202, Yellow No. 4, and Blue No. 404; flavors; balms, and the like.

In order to use the composition of the present invention as the cosmetic material, the composition is processed into the percutaneously administrative agent such as a liquid agent, a solution, an emulsion, a milky liquid, a cream, and a powder or the orally administrative agent such as a solid formulation including a powder, a granule, a capsule, a pill, a tablet, a chewable tablet, and a drop and a liquid agent including a health drink, a solution, a suspension, an emulsion, a syrup, and a dry syrup, for example.

A method of intake in the case of the use as cosmetic material is oral intake or percutaneous intake. The percutaneous intake of a solution, an emulsion, a milky liquid, or a cream is preferred from the viewpoint of an immediate effect.

An amount of intake in the case of the use as cosmetic material may appropriately be decided depending on a symptom. In general, a daily soyasapogenol B intake may preferably be 0.05 to 50 mg, more preferably 0.15 to 10 mg.

EXAMPLES

Hereinafter, examples of the present invention will be described, and the examples do not limit the present invention.

Saponin Analysis Method

Figure 1B:
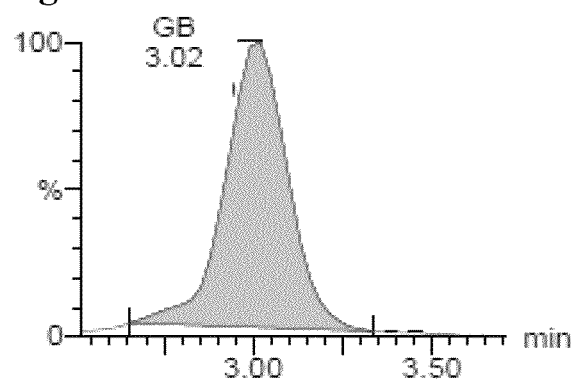
FIG. 1B is a diagram showing a chart of a chromatogram of 3-O-D-glucuronopyranosyl soyasapogenol B (indicated as GB in the drawing)
Figure 1C:
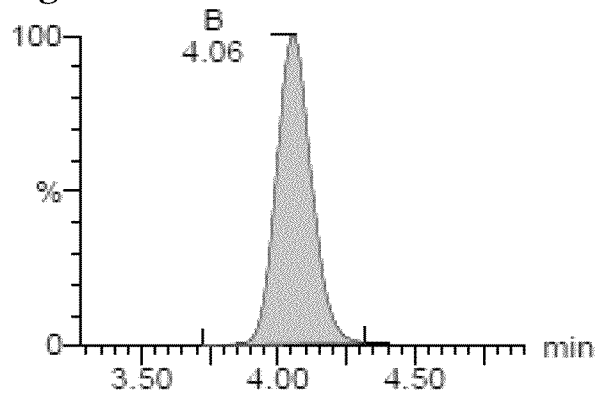
FIG. 1C is a diagram showing a chart of a chromatogram of soyasapogenol B (indicated as B in the drawing)

Saponin was analyzed by a high performance liquid chromatograph tandem quadrupole type mass spectrometer (product of Nihon Waters K. K.). Chromatograms of the soyasapogenol A, 3-O-D-glucuronopyranosyl soyasapogenol B, and soyasapogenol B are respectively shown in FIG. 1A to FIG. 1C. The spectrometry conditions are as follows.

1. Spectrometry Conditions
   Column: 2.1 mmϕ×150 mm (product name: Waters Acquity UPLC RP 18, product of Nihon Waters K. K.)
   Column temperature: 40° C.
   Mobile phase: methanol/water=90/10 (v/v)
   Flow rate: 0.200 mL/min
   Input amount: 5 μL
2. Elution Time and Mass Fragment
   Soyasapogenol A: 3.6 minutes m/z=441 $[M+H-H_2O]^+$
   3-O-D-Glucuronopyranosyl Soyasapogenol B: 3.0 minutes m/z=635 $[M+H]^+$
   Soyasapogenol B: 4.1 minutes m/z=458 $[M+H-H_2O]^+$ Examples 1 to 2

1. Preparation of Soyasapogenol Composition

A 5000 ml glass container was charged with 50 g of soyasaponin glycoside (product name: Saponin AZ-B, product of J-OIL MILLS, INC.) containing 23.2 wt % of saponin group A glycoside and 53.0 wt % of saponin group B glycoside, and then the soyasaponin glycoside was dissolved into 1600 ml of 80% ethanol. Concentrated sulfuric acid was added to the obtained solution so that a sulfuric acid concentration became 2N. The obtained reaction solution was retained at 70° C. to start an acid decomposition reaction of the saponin glycoside.

After the start of the reaction, 150 mL of the reaction solution was collected every hour for 8 hours and neutralized with 1N NaOH. A cake obtained by centrifugation of each of the neutralized product was washed with water and then dried in Yamato Vacuum Drying Oven DP-301 (product of Yamato Scientific Co., Ltd.) to obtain a powder. The composition of Example 1 was prepared by mixing 1.07 g of the powder obtained by 2 hours of the reaction and 1.43 g of the powder obtained by 3 hours of the reaction. The composition of Example 2 was prepared by mixing 1.6 g of the powder obtained by 5 hours of the reaction and 0.6 g of the powder obtained by 6 hours of the reaction. Also, pure soyasapogenol B (purity: 98%, product of Tokiwa Phytochemical Co., Ltd., B/A=0) was used as Comparative Example 1. Constitutions of the compositions of Examples 1 and 2 and Comparative Example 1 were measured by HPLC-MS. The analysis values are shown in Table 1.

TABLE 1

| | Composition | | | | (A) + (B) (in | |
| | Component (A)* (wt %) | Component (B)* (wt %) | Component (C)* (wt %) | (A) + (B) (wt %) | terms of soyasapogenol: wt %) | Weight Ratio (B)/(A) |
| --- | --- | --- | --- | --- | --- | --- |
| Ex. 1 | 15.6 | 15.8 | 5.1 | 31.4 | 27.0 | 1.0 |
| Ex. 2 | 27.1 | 8.9 | 9.4 | 36.0 | 33.5 | 0.33 |

TABLE 1-continued

| | Composition | | | (A) + (B) | (A) + (B) (in terms of soyasapogenol: wt %) | Weight Ratio (B)/(A) |
|---|---|---|---|---|---|---|
| | Component (A)* (wt %) | Component (B)* (wt %) | Component (C)* (wt %) | (A) + (B) (wt %) | | |
| Comp. Ex. 1 | 98.0 | 0.0 | 0.0 | 98.0 | 98.0 | 0 |

(A) soyasapogenol B
(B) 3-O-D-glucuronopyranosyl soyasapogenol B
(C) soyasapogenol A 2. Evaluation of Absorption of Soyasapogenol Composition 5-week-old male SD rats (Charles River Laboratories Japan, Inc.) were divided into groups so that one group consists of 3 to 4 rats. Each of the compositions of Examples 1 and 2 and the pure soyasapogenol B of Comparative Example 1 was suspended into a 0.5% carboxymethyl cellulose sodium (CMC) solution, and a single dose of the suspension in an equivalent amount (100 μmol/kg body weight) in terms of aglycone of the components (A) and (B) was administered to each of the rats with a feeding needle. Blood sampling was conducted at 2 hours after the administration, and plasma was obtained from each of the blood samples.

To each of the obtained plasma, 0.2 M Na acetate buffer solution (pH 5.5) in an amount same as that of the plasma was added. Subsequently, 3000 units of β-glucuronidase (product name: H-2, product of Sigma-Aldrich, Co. LLC) were added, and an enzyme reaction was allowed at 37° C. for 12 hours. After termination of the reaction, 3 ml of a mixture liquid of methanol:acetonitrile (1:1) and internal standard formononetin (product of Sigma-Aldrich, Co. LLC) were added to the enzyme treatment solution, followed by centrifugation, and then a supernatant was collected. An operation of adding 3 ml of the mixture liquid of methanol:acetonitrile (1:1) to a residue and performing centrifugation was repeated twice, and a supernatant was collected after each of the operations. The collected supernatants were mixed and subjected to drying under reduced pressure using a rotary evaporator.

Figure 2:
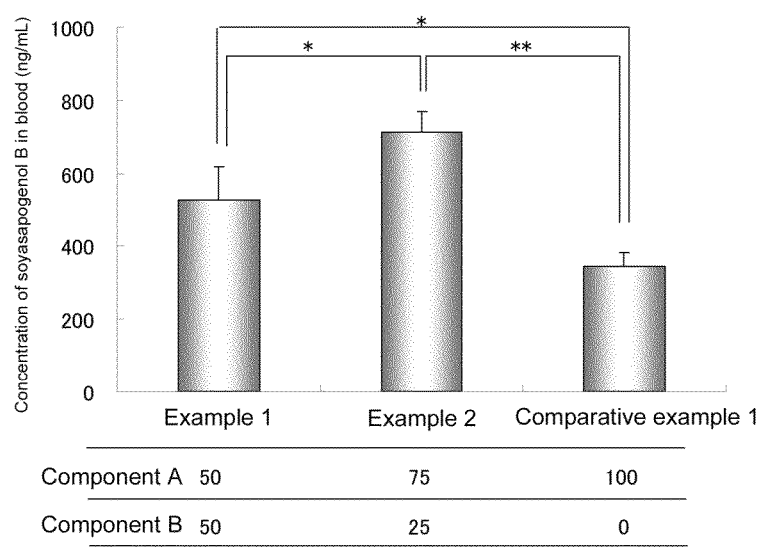
FIG. 2 is a diagram showing blood sapogenol B concentrations which were detected at 2 hours after administration of the compositions of the present invention and pure soyasapogenol B of Comparative Examples to SD rats. The blood soyasapogenol B concentrations of Examples 1 and 2 using the compositions containing the component (B) are significantly higher than Comparative Example 1 using the component (A) alone.

The dried product was dissolved into methanol again, and a blood saponin concentration was examined by HPLC-MS (N=3 or 4). The blood saponin concentrations of the groups are shown in FIG. 2. Statistical analysis was performed by performing the Tukey's multiple comparison test as a significance test. The significant differences having significance levels of <0.05 and <0.01 are respectively indicated by * and ** in the drawing.

As shown in FIG. 2, the blood concentrations of soyasapogenol B of Examples 1 and 2 are significantly higher than Comparative Example 1 for which the 3-O-D-glucuronopyranosyl soyasapogenol B was not used.

Though the concentration of 3-O-D-glucuronopyranosyl soyasapogenol B in the composition of Example 1 is higher than that of Example 2, the blood concentration of soyasapogenol B of Example 2 is higher than that of Example 1. From this result, it is confirmed that the blood concentration of soyasapogenol B does not depend on the concentration of the 3-O-D-glucuronopyranosyl soyasapogenol B.

Examples 3 to 4

1. Preparation of Soyasapogenol Composition

Soyasaponin glycoside was subjected to the partial acid decomposition in the same manner as in Example 1 except for changing the soyasaponin glycoside to Saponin AZ-B (product of J-OIL MILLS, INC.) containing 31.9 wt % of saponin group A glycoside and 60.0 wt % of saponin group B glycoside.

After the start of the reaction, 300 mL of the reaction solution was collected at 3 hours (Example 3) and 6 hours (Example 4) and neutralized with a 1N NaOH solution. A cake obtained by centrifugation of each of the neutralized products was dried in Yamato Vacuum Drying Oven DP-301 (product of Yamato Scientific Co., Ltd.) to obtain a powder. The analysis values of the compositions of Examples 3 and 4 are shown in Table 2.

TABLE 2

| | Acid Decomposition Time (hr) | Component (A)* (wt %) | Component (B)* (wt %) | Component (C)* (wt %) | (A) + (B) (wt %) | (A) + (B) (in terms of soyasapogenol: wt %) | Weight Ratio (B)/(A) |
|---|---|---|---|---|---|---|---|
| Ex. 3 | 3 | 17.0 | 14.2 | 5.5 | 31.2 | 27.3 | 0.84 |
| Ex. 4 | 6 | 33.3 | 10.1 | 9.8 | 43.4 | 40.6 | 0.30 |

(A) soyasapogenol B
(B) 3-O-D-glucuronopyranosyl soyasapogenol B
(C) soyasapogenol A 2. Evaluation of Absorption of Soyasapogenol Composition 8-week-old male SD rats (Charles River Laboratories Japan, Inc.) were divided into groups so that one group consists of 4 rats, and each of the compositions of Examples 3 and 4 and Comparative Example 1 was suspended into a 0.5% CMC solution, followed by a single dose administration of the suspension in an equivalent amount (100 μmol/kg body weight) in terms of saponin aglycone to each of the rats with a feeding needle. Blood sampling was conducted at 1, 3, 8 and 12 hours after the administration, and plasma was obtained from each of the blood samples. Each of the obtained plasma was subjected to the pre-treatment and the HPLC-MS analysis in the same manner as in Example 1 to examine the soyasapogenol B concentration in the blood. The blood soyasapogenol B concentration at 1 to 12 hours after the administration and AUCs (areas under curve of the blood concentration) are shown in Table 3.

TABLE 3

| | Blood Soyasapogenol B Concentration (ng/mL) | | | | |
|---|---|---|---|---|---|
| | 1 hour after | 3 hours after | 8 hours after | 12 hours after | AUC (ng · h/mL) |
| Ex. 3 | 1975.6 | 509.7 | 301.8 | 74.7 | 6254.9 |
| Ex. 4 | 920.0 | 498.3 | 253.2 | 92.1 | 4447.7 |
| Comp. Ex. 1 | 317.4 | 280.2 | 292.6 | 68.1 | 2909.7 |

As shown in Table 3, AUCs, which are indexes of absorption, of Examples 3 and 4 each containing soyasapogenol B and 3-O-D-glucuronopyranosyl soyasapogenol B are higher than that of Comparative Example 1 using soyasapogenol B alone.

Examples 5 to 10

1. Preparation of Soyasapogenol Composition

A 3000 ml glass container was charged with 150 g of soyasaponin glycoside used in Example 3, and the glycoside was dissolved into 1500 ml of 80% ethanol. Concentrated sulfuric acid was added to the obtained solution so that a sulfuric acid concentration became 2N. The solution was retained at 80° C. for 72 hours with the solution slowly stirred to allow partial acid decomposition of the saponin glycoside.

100 ml of the reaction solution was collected before the start of the reaction and after the reaction as shown in Table 3, and each of the collected reaction solutions was neutralized with a 1N NaOH solution. The neutralized products were dried by the evaporator to obtain powders. Analysis values of the obtained compositions are shown in Table 3.

2. Evaluation of Absorption of Soyasapogenol Composition 5-week-old male SD rats (Charles River Laboratories Japan, Inc.) were divided into groups so that one group consists of 3 rats. Each of the compositions shown in Table 3 was suspended into 0.5% CMC solution, and a single dose of the suspension in an equivalent amount (150 µmol/kg body weight) in terms of aglycone of the components (A) and (B) was administered to each of the rats with a feeding needle. Blood sampling was conducted at 2 hours and 4 hours after the administration, and a heparin sodium blood plasma was obtained from each of the blood samples.

Analysis of saponin concentrations of the obtained plasma was conducted in the same manner as in Example 1. From each of the blood saponin concentrations after 2 hours and after 4 hours, AUC (0-4 hour) was detected. Further, relative values of Examples and Comparative Example shown in Table 4 were calculated by setting the AUC including the reaction time=0 when the composition (only glycoside) was administered to 100, and the relative values are used as absorbability indexes. The results are shown in Table 4.

TABLE 4

| | Acid Decomposition Time (hr) | Composition | | | (A) + (B) (wt %) | (A) + (B) (in terms of soyasapogenol: wt %) | Weight Ratio (B)/(A) | Absorbability Index |
|---|---|---|---|---|---|---|---|---|
| | | Component (A)* (wt %) | Component (B)* (wt %) | Component (C)* (wt %) | | | | |
| Ex. 5 | 1 | 3.05 | 7.66 | 1.25 | 10.71 | 8.59 | 2.51 | 2407 |
| Ex. 6 | 2 | 6.53 | 9.20 | 2.48 | 15.73 | 13.18 | 1.41 | 2597 |
| Ex. 7 | 3 | 9.37 | 8.39 | 3.39 | 17.76 | 15.43 | 0.90 | 2832 |
| Ex. 8 | 6 | 14.83 | 4.02 | 5.05 | 18.85 | 17.73 | 0.27 | 1817 |
| Ex. 9 | 16 | 20.22 | 1.41 | 6.96 | 21.63 | 21.24 | 0.014 | 949 |
| Ex. 10 | 23 | 19.21 | 0.02 | 6.90 | 19.23 | 19.22 | 0.001 | 920 |
| Comp. Ex. 2 | 72 | 17.62 | 0 | 6.71 | 17.62 | 17.62 | 0 | 782.3 |

(A) soyasapogenol B
(B) 3-O-D-glucuronopyranosyl soyasapogenol B
(C) soyasapogenol A
Absorbability index = AUC of each of the examples/AUC of the composition (only glycoside) at reaction time = 0 × 100

As shown in Table 4, the compositions (Examples 5 to 10) each containing soyasapogenol B and 3-O-D-glucuronopyranosyl soyasapogenol B have higher blood concentration and higher absorption as compared to Comparative Example 2 which contains soyasapogenol B alone. Also, from the absorbability indexes of Table 4, it is confirmed that the range of B/A may preferably be 0.01 to 5, more preferably 0.01 to 3, furthermore preferably 0.1 to 2.5, most preferably 0.25 to 2.5.

Examples 11 to 13

Preparation of Soyasapogenol Composition

A 50 ml eggplant-shaped flask was charged with 100 mg of a soyasaponin glycoside (product name: J-Saponin, product of J-OIL MILLS, INC.) containing 61.0 wt % of saponin group A glycoside and 30.0 wt % of saponin group B glycoside, and the glycoside was dissolved by adding thereto 10 ml of a 6N sulfuric acid solution. The solution was retained at 80° C. to start acid decomposition reaction of the saponin glycoside.

A whole of the reaction solution was collected at 2 hours, 4 hours, and 8 hours after the start of the reaction. Neutralization with 1N NaOH solution was conducted. Cakes obtained by subjecting the neutralized products to centrifugation were dried in Yamato Vacuum Drying Oven DP-301 (product of Yamato Scientific Co., Ltd.) to obtain powders. Analysis values of the obtained compositions are shown in Table 5.

TABLE 5

| | Acid Decomposition Time (hr) | Composition | | | (A) + (B) (wt %) | (A) + (B) (in terms of soyasapogenol: wt %) | Weight Ratio (B)/(A) |
| | | Component (A)* (wt %) | Component (B)* (wt %) | Component (C)* (wt %) | | | |
| --- | --- | --- | --- | --- | --- | --- | --- |
| Ex. 11 | 2 | 5.8 | 19.4 | 3.5 | 24.7 | 19.8 | 3.3 |
| Ex. 12 | 4 | 9.8 | 15.3 | 5.6 | 25.1 | 20.8 | 1.6 |
| Ex. 13 | 8 | 13.3 | 9.4 | 8.0 | 22.7 | 20.1 | 0.7 |

(A) soyasapogenol B
(B) 3-O-D-glucuronopyranosyl soyasapogenol B
(C) soyasapogenol A Examples 14 to 17

Preparation of Soyasapogenol Composition

A 50 ml eggplant-shaped flask was charged with 100 mg of soyasaponin glycoside (product name: Saponin AZ-B, product of J-OIL MILLS, INC.) containing 12.9 wt % of saponin group A glycoside and 61.6 wt % of saponin group B glycoside, and the glycoside was dissolved by adding thereto 10 ml of 1N hydrochloric acid solution. The solution was retained at 80° C. to start acid decomposition reaction of the saponin glycoside.

A whole of the reaction solution was collected at 1 hour, 8 hours, 16 hours, and 24 hours after the start of the reaction. Neutralization with 1N NaOH solution was conducted. Cakes obtained by subjecting the neutralized products to centrifugation were dried in Yamato Vacuum Drying Oven DP-301 (product of Yamato Scientific Co., Ltd.) to obtain powders. Analysis values of the obtained compositions are shown in Table 6.

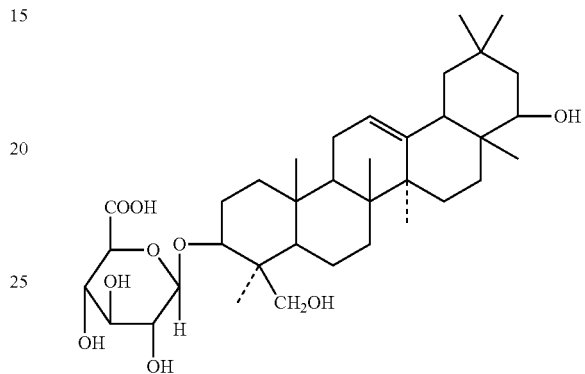

wherein a weight ratio (B/A) of the component (B) to the component (A) is 0.001 to 10.

TABLE 6

| | Acid Decomposition Time (hr) | Composition | | | (A) + (B) (wt %) | (A) + (B) (in terms of soyasapogenol: wt %) | Weight Ratio (B)/(A) |
| | | Component (A)* (wt %) | Component (B)* (wt %) | Component (C)* (wt %) | | | |
| --- | --- | --- | --- | --- | --- | --- | --- |
| Ex. 14 | 1 | 0.07 | 0.25 | 0.09 | 0.32 | 0.25 | 3.57 |
| Ex. 15 | 8 | 1.33 | 2.46 | 0.94 | 3.79 | 3.11 | 1.85 |
| Ex. 16 | 16 | 2.94 | 7.55 | 1.54 | 10.49 | 8.40 | 2.57 |
| Ex. 17 | 24 | 3.82 | 9.40 | 1.97 | 13.22 | 10.61 | 2.46 |

(A) soyasapogenol B
(B) 3-O-D-glucuronopyranosyl soyasapogenol B
(C) soyasapogenol A

What is claimed:

1. A soyasapogenol composition comprising: soyasapogenol B represented by the following Formula A:

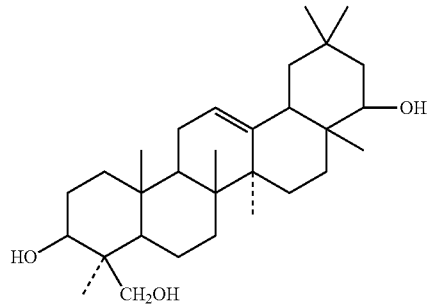

and 3-O-D-glucuronopyranosyl soyasapogenol B represented by the following Formula B:

2. The soyasapogenol composition according to claim 1, wherein the component (A) and the component (B) are provided in an amount of 0.05 to 100 wt % of the soyasapogenol composition.

3. A process for producing the soyasapogenol composition according to claim 1, comprising partially decomposing a sugar chain residue of soyasaponin group B glycoside with acid at a temperature from a room temperature to 80° C.

4. The process according to claim 3, wherein the partially decomposing comprises partially decomposing a material containing at least 5 wt % of soyasaponin group B glycoside.

5. A food or a supplement comprising the soyasapogenol composition according to claim 1.

6. A cosmetic material comprising the soyasapogenol composition according to claim 1.

7. The process according to claim 3, wherein the soyasaponin group B glycoside has the formula:

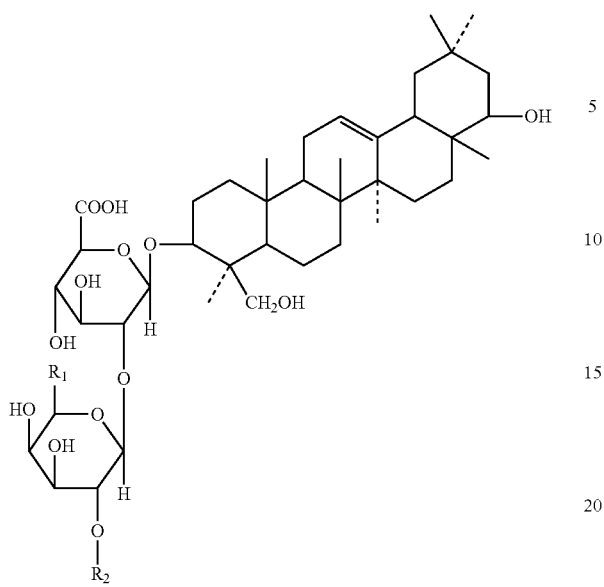
wherein:
 R$_1$ is one of H and CH$_2$OH;
 R$_2$ is one of H, β-D-Glc and α-L-Rha when R$_1$ is CH$_2$OH;
 R$_2$ is one of H and α-L-Rha when R$_1$ is H;
 Glc is glucose; and
 Rha is rhamnose.
* * * * *